(12) United States Patent
Kronenthal et al.

(10) Patent No.: US 7,074,921 B2
(45) Date of Patent: Jul. 11, 2006

(54) PROCESS FOR THE PREPARATION OF 3,7-DISUBSTITUTED-2,3,4,5-TETRAHYDRO-1H-1,4-BENZODIAZEPINE COMPOUNDS

(75) Inventors: David R. Kronenthal, Yardley, PA (US); Rao S. Bhandaru, Belle Mead, NJ (US); Zhongping Shi, West Windsor, NJ (US); Boguslaw M. Mudryk, East Windsor, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 181 days.

(21) Appl. No.: 10/292,093

(22) Filed: Nov. 12, 2002

(65) Prior Publication Data

US 2003/0162965 A1 Aug. 28, 2003

Related U.S. Application Data

(60) Provisional application No. 60/350,674, filed on Nov. 13, 2001.

(51) Int. Cl.
*C07D 243/14* (2006.01)
*A61K 31/55* (2006.01)
*A61P 35/00* (2006.01)

(52) U.S. Cl. ............... 540/569; 540/573; 540/574; 514/221

(58) Field of Classification Search ............... 514/221; 540/569, 573, 574
See application file for complete search history.

(56) References Cited

U.S. PATENT DOCUMENTS

| 5,141,851 A | 8/1992 | Brown et al. ............... 435/15 |
| 6,011,029 A | 1/2000 | Ding et al. ............... 514/221 |
| 6,100,395 A | 8/2000 | Chen et al. ............... 540/504 |
| 6,218,375 B1 * | 4/2001 | Raghavan et al. ............. 514/58 |
| 6,455,523 B1 | 9/2002 | Ding et al. ............... 514/221 |
| 6,458,783 B1 * | 10/2002 | Ding et al. ............... 514/220 |
| 6,537,988 B1 * | 3/2003 | Lee ........................... 514/221 |
| 2002/0169313 A1 * | 11/2002 | Gao et al. ................... 540/484 |

FOREIGN PATENT DOCUMENTS

| EP | 0 675 112 | 10/1995 |
| JP | 7-112930 | 5/1995 |
| WO | WO 95/09001 | 4/1995 |
| WO | WO 95/10514 | 4/1995 |
| WO | WO 95/10515 | 4/1995 |
| WO | WO 95/10516 | 4/1995 |
| WO | WO 99/18951 | 4/1999 |

OTHER PUBLICATIONS

CA 136:355252, 2002.*
Hunt et al., Discovery of (R)-7-Cyano-2,3,4,5-tetrahydro-1-(1H-imidazol-4-ylmethyl)-3-(phenylmethyl)-4-(2-thienylsulfonyl)-1H-1,4-benzodiazepine (BMS-214662), Journal of Medicinal Chemistry, vol. 43, No. 20, pp. 3587-3595, Oct. 5, 2000.*
Rose et al., Preclinical Antitumor Activity of BMS-214662, a Highly Apoptotic and Novel Farnesyltransferase Inhibitor, Cancer Research, vol. 61, No. 20, pp. 7507-7517, Oct. 15, 2001.*
Buchwald, H. et al., "Long-term, continuous intravenous heparin administration by an implantable infusion pump in ambulatory patients with recurrent venous thrombosis", Surgery, vol. 88, No. 4, pp. 507-516 (1980).
Clarke, S., "Protein Isoprenylation and Methylation at Carboxyl-Terminal Cysteine Residues", Annu. Rev. Biochem., vol. 61, pp. 355-386 (1992).
During, M.J. et al., "Controlled Release of Dopamine from a Polymeric Brain Implant: In Vivo Characterization", Ann. Neurol., vol. 25, pp. 351-356 (1989).
Glenn, J.S. et al., "Identification of a Prenylation Site in Delta Virus Large Antigen", Science, vol. 256, pp. 1331-1333 (1992).
Goodson, J.M., Chapter 6: "Dental Applications", Medical Applications of Controlled Release, vol. II: Applications and Evaluation, CRC Press, Inc., publ., Langer, R.S. et al., eds., pp. 115-138 (1984).
Graham, S.L. et al., "Pseudopeptide Inhibitors of Ras Farnesyl-Protein Transferase", J. Med. Chem., vol. 37, pp. 725-732 (1994).
Howard III, M.A. et al., "Intracerebral drug delivery in rats with lesion-induced memory deficits", J. Neurosurg., vol. 71, pp. 105-112 (1989).
James, G.L. et al., "Benzodiazepine Peptidomimetics: Potent Inhibitors of Ras Farnesylation in Animal Cells", Science, vol. 260, pp. 1937-1942 (1993).
James, G.L. et al., "PxF, a Prenylated Protein of Peroxisomes", The Journal of Biological Chemistry, vol. 269, No. 19, pp. 14182-14190 (1994).
Kohl, N.E. et al., "Inhibition of farnesyltransferase induces regression of mammary and salivary carcinomas in *ras* transgenic mice", Nature Medicine, vol. 1, No. 8, pp. 792-797 (1995).
Kohl, N.E. et al., "Protein farnesyltransferase inhibitors block the growth of *ras*-dependent tumors in nude mice", Proc. Natl. Acad. Sci. USA, vol. 91, pp. 9141-9145 (1994).
Kohl, N.E. et al., "Selective Inhibition of *ras*-Dependent Transformation by a Farnesyltransferase Inhibitor", Science, vol. 260, pp. 1934-1937 (1993).

(Continued)

*Primary Examiner*—Brenda Coleman
(74) *Attorney, Agent, or Firm*—Jacqueline M. Cohen; Deanna L. Baxam

(57) ABSTRACT

Methods for the synthesis of benzodiazepine compounds having farnesyl protein transferase inhibitory activity.

11 Claims, No Drawings

OTHER PUBLICATIONS

Langer, R., "New Methods of Drug Delivery", Science, vol. 249, pp. 1527-1533 (1990).

Langer, R. et al., "Chemical and Physical Structure of Polymers as Carriers for Controlled Release of Bioactive Agents: A Review", JMS-Rev. Macromol. Chem. Phys., C23, No. 1, pp. 61-126 (1983).

Langer, R.S. et al., eds., Medical Applications of Controlled Release, vol. I: Classes of Systems, and vol. II: Applications and Evaluation, CRC Press, Inc., publ. (table of contents) (1984).

Levy, R.J. et al., "Inhibition of Calcification of Bioprosthetic Heart Valves by Local Controlled-Release Diphosphonate", Science, vol. 228, pp. 190-192 (1985).

Lowy, D.R. et al., "Function and Regulation of RAS", Annu. Rev. Biochem., vol. 62, pp. 851-891 (1993).

Reiss, Y. et al., "Sequence requirement for peptide recognition by rat brain p21$^{ras}$ protein farnesyltransferase", Proc. Natl. Acad. Sci. USA, vol. 88, pp. 732-736 (1991).

Saudek, C.D. et al., "A Preliminary Trial of the Programmable Implantable Medication System for Insulin Delivery", The New England Journal of Medicine, vol. 321, No. 9, pp. 574-579 (1989).

Schafer, W.R. et al., "Protein Prenylation: Genes, Enzymes, Targets, and Functions", Annu. Rev. Genet., vol. 30, pp. 209-237 (1992).

Sefton, M.V., "Implantable Pumps", CRC Critical Reviews in Biomedical Engineering, vol. 14, No. 3, pp. 201-240 (1987).

Smolen, V.F. et al., eds., Controlled Drug Bioavailability, vol. 1: Drug Product Design and Performance, John Wiley & Sons, publ., pp. xiii (table of contents) (1984).

Smolen, V.F. et al., eds., Controlled Drug Bioavailability, vol. 2: Bioavailability Methodology and Regulation, John Wiley & Sons, publ., pp. xiii (table of contents) (1984).

Willumsen, B.M. et al., "The p21 *ras* C-terminus is required for transformation and membrane association", Nature, vol. 310, pp. 583-586 (1984).

Chen, B., et al., "Novel triethylsilane mediated reductive N-alkylation of amines: improved synthesis of 1-(4-imidazolyl)methyl-4-sulfonylbenzodiazepines, new farnesyltransferase inhibitors", Tetrahedron Letters, vol. 42, pp. 1245-12-46, (2001).

\* cited by examiner

US 7,074,921 B2

PROCESS FOR THE PREPARATION OF 3,7-DISUBSTITUTED-2,3,4,5-TETRAHYDRO-1H-1,4-BENZODIAZEPINE COMPOUNDS

This application claims a benefit of priority based on U.S. provisional application 60/350,674, filed Nov. 13, 2001, the entire disclosure of which is herein incorporated by reference.

FIELD OF THE INVENTION

This invention relates to methods for the synthesis of 3,7-disubstituted-2,3,4,5-tetrahydro-1H-1,4-benzodiazepine compounds, particularly to methods in which the use of hazardous starting materials and reagents is avoided or minimized.

BACKGROUND OF THE INVENTION

The Ras proteins (Ha-Ras, Ki4a-Ras, Ki4b-Ras and N-Ras) are part of a signaling pathway that links cell surface growth factor receptors to nuclear signals initiating cellular proliferation. Biological and biochemical studies of Ras action indicate that Ras functions like a G-regulatory protein. In the inactive state, Ras is bound to guanosine diphosphate (GDP). Upon growth factor receptor activation Ras is induced to exchange GDP for guanosine triphosphate (GTP) and undergoes a conformational change. The GTP-bound form of Ras propagates the growth stimulatory signal. The signal is terminated by the intrinsic GTPase activity of Ras, facilitated by the GTPase activating protein (GAP), which returns the protein to its inactive GDP bound form (D. R. Lowy and D. M. Willumsen, Ann. Rev. Biochem. 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GAP-assisted GTPase activity and transmit an uncontrolled growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., (J. Biol. Chem. 269, 14182 (1994)) have identified a peroxisome associated protein, Pxf, which is also farnesylated. James, et al. have also suggested that there are farnesylated proteins of unknown structure and function in addition to those listed above.

Inhibition of farnesyl-protein transferase (FPTase) has been shown to block the growth of Ras-transformed cells in soft agar and to modify other aspects of their transformed phenotype. It has also been demonstrated that certain inhibitors of FPTase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of FPTase blocks the growth of ras-dependent tumors in nude mice (N. E. Kohl et al., Proc. Natl. Acad. Sci U.S.A., 91:9141–9145 (1994)) and induces regression of mammary and salivary carcinomas in ras transgenic mice (N. E. Kohl et al., Nature Medicine, 1:792–797 (1995)).

It has also been reported that FPTase inhibitors are also inhibitors of proliferation of vascular smooth muscle cells and are, therefore, useful in the prevention and therapy of arteriosclerosis and diabetic disturbance of blood vessels (Japanese Patent H7-112930).

Inhibitors of FPTase have been classified in two general classes. The first are analogs of farnesyl diphosphate (FPP), while the second class of inhibitors is structurally related to the enzyme's protein substrates (e.g., Ras). The peptide derived inhibitors that have been described are generally cysteine-containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the FPTase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been disclosed that certain tricyclic compounds which optionally incorporate a piperidine moiety are inhibitors of FPTase (WO 95/10514, WO 95/10515 and WO 95/10516). Imidazole-containing inhibitors of FPTase have also been disclosed (WO 95/09001 and EP 0 675 112 A1). A number of benzodiazepine-based FPTase inhibitors are also described in U.S. Pat. No. 6,011,029, which is commonly assigned with this application.

There is, therefore, a need for a variety of pharmaceutically useful FPTase inhibitors, as well as for safer and more efficient processes for their manufacture.

SUMMARY OF THE INVENTION

The present invention provides a process for the preparation of 3,7-disubstituted-2,3,4,5-tetrahydro-1H-1,4-benzodiazepine compounds. The process of the invention avoids or minimizes the use of hazardous reagents or starting materials, such as boranes and cyanides, as used in the process described in U.S. Pat. No. 6,011,029, which is commonly assigned with this application.

The process of the invention comprises, in one aspect, the steps of reacting a substituted o-nitrobenzaldehyde with a β-hydroxyalkyl amine to form the corresponding Schiff's base, reducing the resulting Schiff's base to form a secondary amine, reacting the β-hydroxyl group of the resulting secondary amine with a silyl protecting agent, acylating or sulfonylating the secondary amine, deprotecting the β-hydroxyl group, sulfonylating the deprotected β-hydroxyl group, reducing the nitro group to an amine group, and reacting the resulting compound with a base to close the diazepine ring. Optionally, the resulting benzodiazepine may be reacted further with an aldehyde under reductive alkylation conditions. The process may also be modified by reacting the β-hydroxyl silyl protected secondary amine with aldehyde before completing the ring-closing step.

In another aspect, the invention provides a process for reacting a substituted N-(2-aminophenylmethyl)-N-(2-sulphonyloxyethyl)-amine with a base to form a benzodiazepine, and optionally reacting the benzodiazepine with an aldehyde under reductive alkylation conditions.

In yet another aspect, compounds which may be reacted further according to the processes of the invention to form substituted benzodiazepines are provided.

The present invention also provides compounds made by the processes of the invention, methods for treating diseased mammals using compounds made by the processes of the invention, and pharmaceutical compositions comprising compounds made by the processes of the invention.

DETAILED DESCRIPTION OF PREFERRED EMBODIMENTS OF THE INVENTION

Accordingly, in a first aspect, the present invention provides a step-wise process for the preparation of a compound of formula I

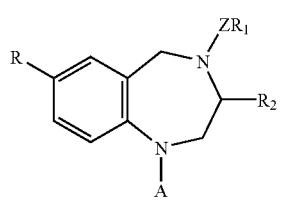

(I)

and salts, solvates, enantiomers and diastereomers thereof wherein

R is Cl, Br, CN, optionally substituted phenyl or optionally substituted 2-, 3- or 4-pyridyl;

$R_1$ is optionally substituted lower alkyl, optionally substituted aryl or optionally substituted heterocyclo;

$R_2$ is optionally substituted lower alkyl or optionally substituted aralkyl;

Z is CO or $SO_2$;

A is hydrogen or, optionally,

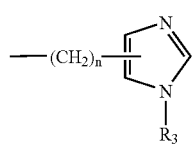

$R_3$ is hydrogen or lower alkyl; and n is 1 or 2, through a series of intermediate compounds, comprising the steps of:

a) reacting a compound of formula II

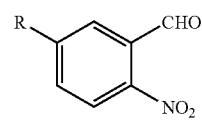

(II)

wherein R is as recited hereinabove, with an amine of formula III

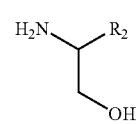

(III)

wherein $R_2$ is as recited hereinabove, to form a compound of formula IV

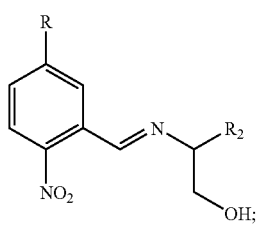

(IV)

b) reacting the formula IV compound with a reducing agent to form a compound of formula V

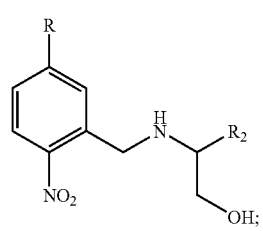

(V)

c) reacting the formula V compound with a silyl protecting agent, optionally in the presence of a base, to form a compound of formula VI

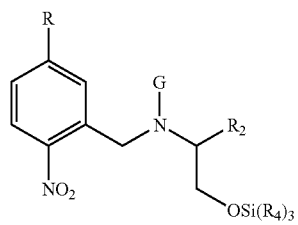

(VI)

wherein $R_4$ is lower alkyl or optionally substituted phenyl and G is H or $Si(R_4)_3$ or a mixture of both H and $Si(R_4)_3$;

d) reacting the formula VI compound with a halide of formula VII

R₁Z-X   (VII)

wherein R₁ and Z are as recited hereinabove and X is a halogen, an acyloxy, or an alkyl sulfonate, to form a compound of formula VIII

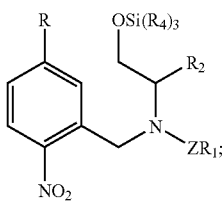

(VIII)

e) reacting the formula VIII compound with a deprotecting agent to form a deprotected compound of formula IX

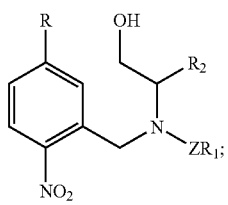

(IX)

f) reacting the formula IX compound with a sulfonyl halide of formula X

R₅SO₂Y   (X)

wherein R₅ is lower alkyl or optionally substituted phenyl and Y is a halogen, in the presence of a base, to form a sulfonylated compound of formula XI

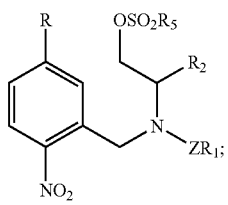

(XI)

g) reducing the nitro substituent of the formula XI compound to form an amino compound of formula XII;

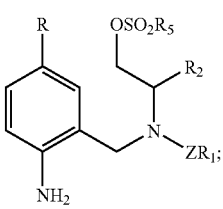

(XII)

h) reacting the formula XII compound with a base to effect a ring closure and produce a compound of formula I, above, wherein A is hydrogen; and i) optionally reacting the formula I compound wherein A is hydrogen with an aldehyde of the formula XIII

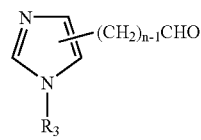

(XIII)

wherein R₃ and n are as recited hereinabove, under reductive alkylation conditions to form a compound of formula I wherein A is

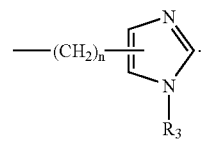

In a preferred embodiment, R is CN; R₁ is optionally substituted lower alkyl, optionally substituted phenyl, optionally substituted 2-thienyl, or optionally substituted 1-piperidinyl; R₂ is optionally substituted benzyl; A is hydrogen or

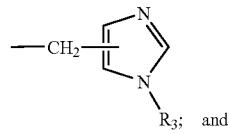

R₃ is hydrogen or methyl.

In a further preferred embodiment, R is CN; R₁ is n-propyl, n-butyl, 3-methoxypropyl, 2-thienyl, 5-bromo-2-thienyl, phenyl, 4-methoxyphenyl or 1-piperidinyl; R₂ is benzyl; Z is SO₂; and A is

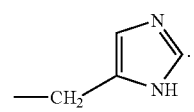

In some preferred embodiments, X and Y are each independently Cl or Br. In other preferred embodiments, X and Y are Cl, and in yet other preferred embodiments, R₄ is lower alkyl and R₅ is optionally substituted phenyl.

In some preferred embodiments, steps (a) and (b) are each independently conducted in the presence of a solvent selected from the group consisting of an aromatic hydrocarbon, a halogenated aromatic hydrocarbon, a halogenated alkane, an ether, including cyclic ethers such as THF, a C₁–C₄alkanoic acid, an N,N-dialkylamide and N-methylpyrrolidinone and mixtures thereof, step (c) is conducted in the presence of a solvent selected from the group consisting of dichloromethane, THF, pyridine, diisopropylethylamine, triethylamine, N-methyl morpholine, N-methyl piperidine and N-methylpyrrolidine and mixtures thereof; step (d) is conducted in the presence of a solvent selected from the group consisting of dichloromethane, THF, pyridine, diisopropylethylamine, triethylamine, N-methyl morpholine, and mixtures thereof; step (e) is conducted in the presence of water or an aqueous acid added to a solvent selected from the group consisting of dichloromethane, THF, pyridine, diisopropyl-ethylamine, triethylamine, N-methyl morpholine, and mixtures thereof; step (f) is conducted in the presence of a solvent selected from the group consisting of a halogenated alkane, an aromatic hydrocarbon, a halogenated aromatic hydrocarbon, an ether, an N,N-dialkylamide, a $C_1$–$C_4$alkyl $C_1$–$C_4$alkanoate and N-methylpyrrolidinone and mixtures thereof; step (g) is conducted in the presence of a solvent selected from the group consisting of a water-miscible solvent and water and mixtures thereof; and step (h) is conducted in the presence of a solvent selected from the group consisting of an ether, an aromatic hydrocarbon, a halogenated aromatic hydrocarbon, a halogenated alkane, an N,N-dialkylamide and N-methylpyrrolidinone and mixtures thereof.

Reductive aminations such as those performed in step (a) are disclosed in commonly assigned U.S. Pat. No. 6,100,395, and U.S. patent application Ser. No. 10/121,014 the entire disclosures of which are herein incorporated by reference.

The reaction of step (f) may be conducted using any suitable sulfonylating agent non-limiting examples of such agents include sulfonyl halides and sulfonic anhydrides.

In some other preferred embodiments, the reducing agent in step (b) is a metal borohydride; the silyl protecting agent in step (c) is selected from the group consisting of a halotrialkylsilane and a bistrialkylsilylacetamide; the deprotecting agent in step (e) is selected from the group consisting of an organic acid, a mineral acid, a base and a fluoride ion source; the base in step (f) is selected from the group consisting of a tri($C_1$–$C_4$alkyl)amine, optionally substituted pyridine and 1,8-diazabicyclo [5.4.0]undec-7-ene; the reducing agent in step (g) is selected from the group consisting of hydrogen in the presence of a catalyst, sodium dithionite, zinc, zinc in the presence of an acid, iron in the presence of an acid and iron in the presence of ammonium chloride; and the base in step (h) is selected from the group consisting of an alkali metal $C_1$–$C_6$ alkoxide, an alkali metal dialkylamide, an alkali metal hydride, an alkali metal carbonate and a tertiary amine base.

In another preferred embodiment, the step (i) reductive alkylation comprises reacting the formula I compound wherein A is hydrogen and the aldehyde of formula XIII with: (1) an alkali metal borohydride in the presence of an acid, or (2) a hydrotrialkylsilane in the presence of an acid.

In some further preferred embodiments, various steps or combinations of steps are performed in situ. The expression "in situ" as used herein refers to any process in which the products of intermediate reactions are not isolated or purified. Advantages of in situ processing include the simplification of operation made possible by not isolating or purifying intermediates. These advantages are especially applicable to the processes of the present invention, in which many of the intermediates are water-sensitive. For example, in a preferred embodiment, steps (a) and (b) are conducted in situ. In another preferred embodiment, steps (c), (d) and (e) are conducted in situ. In yet another preferred embodiment, steps (f), (g) and (h) are conducted in situ. In step (e), or any other step in the process of the invention, the reaction may be carried out in situ despite low miscibility or even phase separation of the various solvents in the reaction mixture.

In another aspect, the invention provides a process for the preparation of a compound of formula I

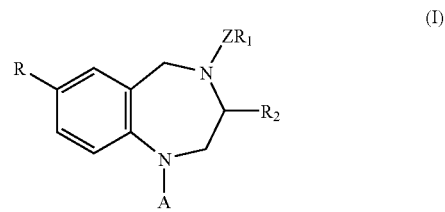

and salts, solvates, enantiomers and diastereomers thereof wherein

R is Cl, Br, CN, optionally substituted phenyl or optionally substituted 2-, 3- or 4-pyridyl;

$R_1$ is optionally substituted lower alkyl, optionally substituted aryl or optionally substituted heterocyclo;

$R_2$ is optionally substituted lower alkyl or optionally substituted aralkyl;

Z is CO or $SO_2$;

A is hydrogen or

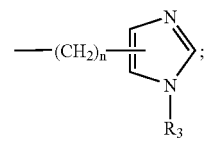

$R_3$ is hydrogen or lower alkyl; and n is 1 or 2, which process comprises the steps of:

a) reacting a compound of formula XII

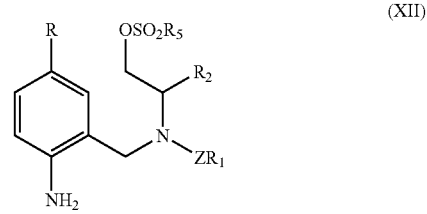

wherein R, $R_1$, $R_2$, and Z are as recited hereinabove with a base to form a compound of formula I wherein A is hydrogen; and b) optionally reacting the product of step a) with an aldehyde of formula XIII

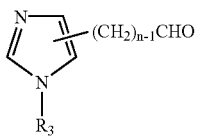
(XIII)

wherein $R_3$ and n are as recited hereinabove, under reductive alkylation conditions to form a compound of formula I wherein A is

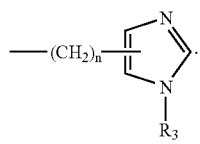

In a preferred embodiment, R is CN; $R_1$ is optionally substituted lower alkyl, optionally substituted phenyl, optionally substituted 2-thienyl, or optionally substituted 1-piperidinyl; $R_2$ is optionally substituted benzyl; A is hydrogen or

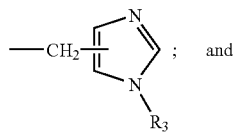 ; and $R_3$ is hydrogen or methyl.

In another preferred embodiment, R is CN; $R_1$ is n-propyl, n-butyl, 3-methoxypropyl, 2-thienyl, 5-bromo-2-thienyl, phenyl, 4-methoxyphenyl or 1-piperidinyl; $R_2$ is benzyl; Z is $SO_2$; and A is hydrogen or

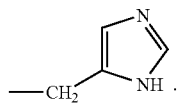

In yet another preferred embodiment, $R_5$ is optionally substituted phenyl.

In some preferred embodiments, step (a) is conducted in the presence of a solvent selected from the group consisting of an ether, an aromatic hydrocarbon, a halogenated aromatic hydrocarbon, a halogenated alkane, an N,N-dialkylamide, N-methylpyrrolidinone and mixtures thereof.

In some other preferred embodiments, the base reacted with the compound of formula XII in step (a) is selected from the group consisting of an alkali metal $C_1$–$C_6$ alkoxide, an alkali metal dialkylamide, an alkali metal hydride, an alkali metal carbonate and a tertiary amine base.

In other preferred embodiments, the step (b) reductive alkylation comprises reacting the formula I compound wherein A is hydrogen and the aldehyde of formula XIII with: (1) an alkali metal borohydride in the presence of an acid, or (2) a hydrotrialkylsilane in the presence of an acid and optionally, a dehydrating agent such as an acid anhydride, as disclosed in commonly assigned U.S. application Ser. No. 10/121,074.

In another aspect, the invention provides a compound selected from the group consisting of those having the structural formulae:

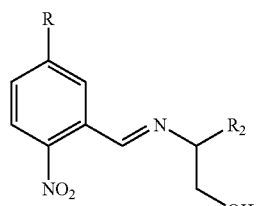
(IV)

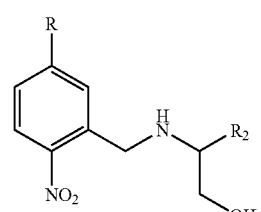
(V)

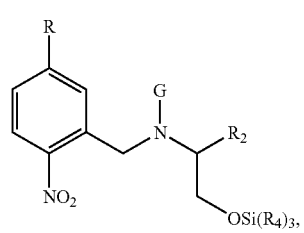
(VI)

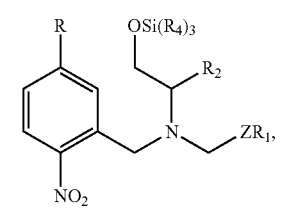
(VIII)

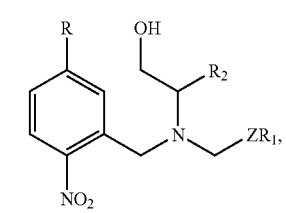
(IX)

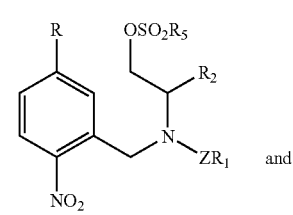
(XI)

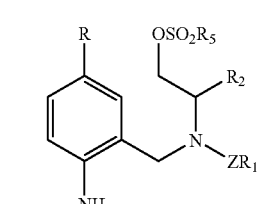
and

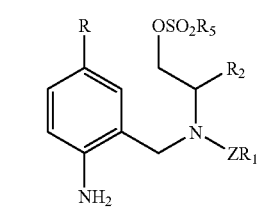
(XII)

and salts, solvates, enantiomers and diastereomers thereof wherein

R is Cl, Br, CN, optionally substituted phenyl or optionally substituted 2-, 3- or 4-pyridyl;

$R_1$ is optionally substituted lower alkyl, optionally substituted aryl or optionally substituted heterocyclo;

$R_2$ is optionally substituted lower alkyl or optionally substituted aralkyl;

G is H or $Si(R_4)_3$ or a mixture of both H and $Si(R_4)_3$;

Z is CO or $SO_2$; and $R_4$ and $R_5$ are each independently lower alkyl or optionally substituted phenyl.

In a preferred embodiment, R is CN; $R_1$ is optionally substituted lower alkyl, optionally substituted phenyl, optionally substituted 2-thienyl or optionally substituted 1-piperidinyl; $R_2$ is optionally substituted benzyl; Z is CO or $SO_2$; $R_4$ is lower alkyl; and $R_5$ is optionally substituted phenyl.

In another preferred embodiment, R is CN; $R_1$ is n-propyl, n-butyl, 3-methoxypropyl, 2-thienyl, 5-bromo-2-thienyl, phenyl, 4-methoxyphenyl or 1-piperidinyl; $R_2$ is benzyl; Z is $SO_2$; $R_4$ is lower alkyl; and $R_5$ is optionally substituted phenyl.

The compounds of formula I may alternatively be prepared via a sequence of processing steps in which after the protected secondary amine of formula XII is reacted with an aldehyde of formula XIII in an addition reaction before the ring-closing step that forms the benzodiazepine.

Accordingly, in this alternate embodiment, intermediates of formula XIV may be formed.

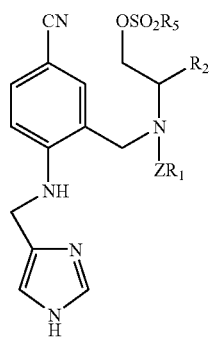

(XIV)

Some especially preferred embodiments of the invention include 3-[[[(1R)-1-(hydroxymethyl)-2-phenylethyl]imino] methyl]-4-nitrobenzonitrile

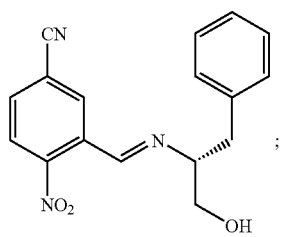

(R)-3-[N-(1-hydroxymethyl-2-phenylethyl)amino]methyl-4-nitrobenzenecarbonitrile

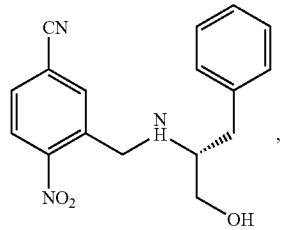

4-nitro-3-[[[(1R)-1-(phenylmethyl)-2-[(trimethylsilyl)oxy] ethyl]amino]methyl]benzonitrile

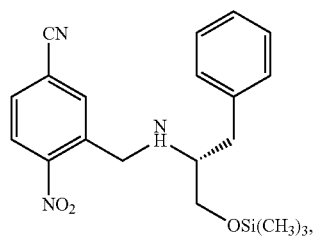

N-[(5-cyano-2-nitrophenyl)methyl]-N-[(1R)-1-(phenylmethyl)-2-[(trimethylsilyl)oxy]ethyl]-2-thiophenesulfonamide

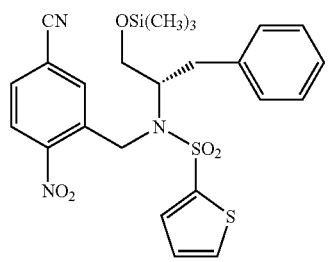

(R)-N-[5-cyano-2-nitrophenyl)methyl]-N-[(1-hydroxymethyl)-2-phenylethyl]thiophene-2-sulfonamide

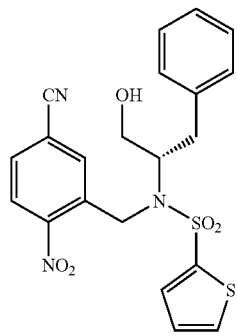

N-[(5-cyano-2-nitrophenyl)methyl]-N-[(1R)-1-(phenylmethyl)-2-[(phenylsulfonyl)oxy]ethyl]-2-thiophene-sulfonamide

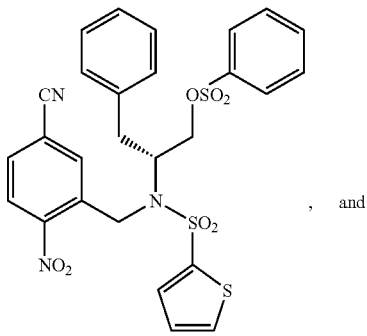

N-[(2-amino-5-cyanophenyl)methyl]-N-[(1R)-1-(phenylmethyl)-2-[(phenylsulphonyl)oxy]ethyl]-2-thiophene-sulfonamide

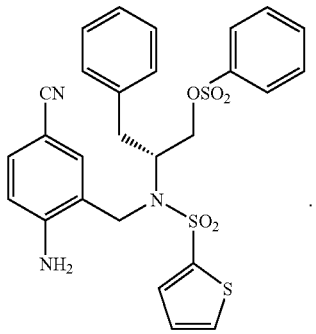

Benzenesulfonic acid 2-[{5-cyano-2-[(1H-imidazol-4-ylmethyl)-amino]-benzyl}-(thiophene-2-sulfonyl)-amino]-3-phenyl-propyl ester

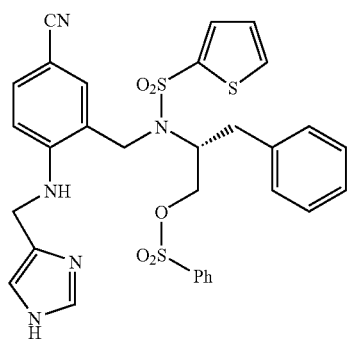

In further aspects, the present invention provides compounds made by the processes of the invention, methods for treating diseased mammals using compounds of formula I, and pharmaceutical compositions comprising compounds of formula I.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, 1 to 39 substituents, preferably 1 to 15 substituents, and most preferably one to four substituents. The substituents may include, without limitation, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2 NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The terms "halogen," "halide" and "halo" refer to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl moiety, such as benzyl. An aralkyl group may be substituted with any group described herein as an aryl or alkyl substituent.

The term "substituted aryl" refers to an aryl group substituted by, for example, one to seven substituents, and, preferably, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to 39 substituents, preferably one to 15 substituents, and most preferably one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. indolyl, imidazolyl, furyl, thienyl, thiazolyl, pyrrolidyl, pyridyl, pyrimidyl and the like.

The term "cycloalkyl" refers to optionally substituted, saturated cyclic hydrocarbon ring systems, preferably containing 1 to 3 rings and 3 to 7 carbons per ring which may be further fused with an unsaturated $C_3-C_7$ carbocylic ring.

Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or non-aromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for heterocyclic groups include one or more alkyl groups as described above or one or more groups described above as alkyl substituents. Also included are smaller heterocyclos, such as epoxides and aziridines.

The term "heteroatoms" includes oxygen, sulfur and nitrogen.

The term "acyloxy" refers to an —O—C(O)-$R_a$ group, wherein $R_a$ is a alkyl, cycloalkyl, alkenyl, aryl, aralkyl, or heterocyclic group. The $R_a$ group may be substituted or unsubstituted. The term "alkanoate" refers to an acyloxy group derived from an alkanoic acid.

Those of skill in the art will recognize that there exist many equivalents for $R_1Z$-X which will produce compounds of formula VIII when reacted with compounds of formula VII. In one preferred embodiment, $R_1Z$-X is a sulfonyl anhydride, wherein X is an alkyl sulfonate or an aryl sulfonate group, for example. In another preferred embodiment, $R_1Z$-X is a hindered mixed acid anhydride, in which X is a neo-pentanoate group, for example. All such equivalents of $R_1Z$-X are included in the scope of the present invention.

As used herein, the expression "optionally substituted," as in "optionally substituted lower alkyl", "optionally substituted aryl" or the like, refers to alkyl, aryl, and other groups which may be unsubstituted or substituted with the substituents mentioned above. Further, when a moiety is described herein as optionally substituted with more than one substituent, it is intended that each of the multiple substituents be chosen independently from among the substituents mentioned above.

Representative examples of compounds of the invention and compounds that can be made by the processes of the invention include:

(R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;

(R)-2,3,4,5-tetrahydro-3-(phenylmethyl)-4-(2-thienylsulfonyl)-1H-1,4-benzodiazepine-7-carbonitrile;

(R)-7-cyano-2,3,4,5-tetrahydro-1-(1H-imidazol-4-ylmethyl)-4-(1-oxobutyl)-3-(phenylmethyl)-1H-1,4-benzodiazepine;

(R)-7-cyano-2,3,4,5-tetrahydro-4-(1-oxobutyl)-3-(phenylmethyl)-1H-1,4-benzodiazepine;

(R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine;

(R)-4-[(5-bromo-2-thienyl)sulfonyl]-7-cyano-2,3,4,5-tetrahydro-3-(phenyl-methyl)-1H-1,4-benzodiazepine;

(R)-7-cyano-2,3,4,5-tetrahydro-1-(1H-imidazol-4-ylmethyl)-4-[(4-methoxy-phenyl)sulfonyl]-3-(phenylmethyl)-1H-1,4-benzodiazepine;

(R)-7-cyano-2,3,4,5-tetrahydro-4-[(4-methoxyphenyl)sulfonyl]-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(phenylsulfonyl)-1H-1,4-benzodiazepine;

(R)-7-cyano-2,3,4,5-tetrahydro-3-(phenylmethyl)-4-(phenylsulfonyl)-1H-1,4-benzodiazepine;

(R)-7-cyano-2,3,4,5-tetrahydro-1-(1H-imidazol-4-ylmethyl)-3-(phenylmethyl)-4-(propylsulfonyl)-1H-1,4-benzodiazepine;

(R)-7-cyano-2,3,4,5-tetrahydro-3-(phenylmethyl)-4-(propylsulfonyl)-1H-1,4-benzodiazepine;

(R)-4-(butylsulfonyl)-7-cyano-2,3,4,5-tetrahydro-1-(1H-imidazol-4-ylmethyl)-3-(phenylmethyl)-1H-1,4-benzodiazepine;

(R)-4-(butylsulfonyl)-7-cyano-2,3,4,5-tetrahydro-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(1-piperidinylsulfonyl)-1H-1,4-benzodiazepine;

(R)-7-cyano-2,3,4,5-tetrahydro-3-(phenylmethyl)-4-(1-piperidinylsulfonyl)-1H-1,4-benzodiazepine;

(R)-4-(3-methoxypropylsulfonyl)-7-cyano-2,3,4,5-tetrahydro-1-(1H-imidazol-4-ylmethyl)-3-(phenylmethyl)-1H-1,4-benzodiazepine;

(R)-4-(3-methoxypropylsulfonyl)-7-cyano-2,3,4,5-tetrahydro-3-(phenylmethyl)-1H-1,4-benzodiazepine; and Benzenesulfonic acid 2-[{5-cyano-2-[(1H-imidazol-4-ylmethyl)-amino]-benzyl}-(thiophene-2-sulfonyl)-amino]-3-phenyl-propyl ester.

Compounds of formula I may form salts, which are also within the scope of this invention. Pharmaceutically acceptable (i.e., non-toxic, physiologically acceptable) salts are preferred, although other salts may also be useful, e.g., in isolating or purifying the compounds of this invention.

Depending on the nature of the substituents, compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if the compound contains a carboxylic acid, with the desired ion in a medium in which the salt precipitates or in an aqueous medium followed by evaporation. Additionally, a salt may be formed by reacting an acid with an amine group, if the compound has an amine group. Other salts can be formed by methods well known to those skilled in the art.

Compounds of formula I may also form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds of formula I with an equivalent amount of the acid in a medium in which the salt precipitates or in an aqueous medium followed by evaporation.

In addition, zwitterions ("inner salts") may be formed.

Isomers of compounds of formula I, such as enantiomers, diastereomers, and tautomers, are also within the scope of the present invention.

Compounds of formula I are inhibitors of FPTase. They are thus useful in the treatment of a variety of cancers, including (but not limited to) the following:

carcinoma, including that of the bladder, breast, colon, kidney, liver, lung, including small cell lung cancer, ovary, prostate, testes, pancreas, esophagus, stomach, gall bladder, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias, myelodysplastic syndrome and promyelocytic leukemia;

tumors of the central and peripheral nervous system, including astrocytoma, neuroblastoma, glioma, and schwannomas;

tumors of mesenchymal origin, including fibrosarcoma, rhabdomyoscarcoma, and osteosarcoma;

other tumors, including melanoma, xenoderma pigmentosum, keratoactanthoma, seminoma, thyroid follicular cancer and teratocarcinoma.

Compounds of formula I are especially useful in treatment of tumors having a high incidence of ras involvement, such as colon, lung, and pancreatic tumors and in tumors in which a prenyl transferase contributes to tumor maintenance, tumor growth or tumor development. By the administration of a composition having one (or a combination) of the compounds made by processes of the invention, development of tumors in a mammalian host is reduced, or tumor burden is reduced, or tumor regression is produced.

Compounds of formula I may also be useful in the treatment of diseases other than cancer that may be associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation, polycystic kidney disease and endotoxic shock.

Compounds of formula I may also be useful in the treatment of diseases associated with farnesyl transferase substrates other than ras (e.g., nuclear lamins, transducin, rhodopsin kinase, cGMP phosphodiesterase, TC21, phosphorylase kinase, Rap2, RhoB, RhoE, PRL1) that are also post-translationally modified by the enzyme FPTase.

Compounds of formula I may also act as inhibitors of other prenyl transferases (e.g., geranylgeranyl transferase I and II), and thus be effective in the treatment of diseases associated with other prenyl modifications (e.g., geranylgeranylation) of proteins (e.g. the rap, rab, rac and rho gene products and the like). For example, they may find use as drugs against hepatitis delta virus (HDV) infections, as suggested by the recent finding that geranylgeranylation of the large isoform of the delta antigen of HDV is a requirement for productive viral infection [J. S. Glen et al., Science, 256, 1331 (1992)].

Compounds of formula I may also be useful in combination with known anti-cancer and cytotoxic agents and treatments, including radiation. If formulated as a fixed dose, such combination products employ the compounds of this invention within the dosage range described below and the other pharmaceutically active agent(s) within their approved dosage ranges. The compounds of formula I may be used sequentially with known anticancer or cytotoxic agents and treatment, including radiation when a combination formulation is inappropriate.

In a further aspect, the present invention provides a pharmaceutical composition comprising at least one compound of formula I and a pharmaceutically acceptable carrier.

The phrase "pharmaceutically acceptable" as used herein refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "carrier" as used herein refers to a diluent, adjuvant, excipient, or vehicle with which a pharmaceutical composition of the present invention is administered. Such pharmaceutical carriers include, without limitation, sterile liquids, such as water, saline, buffered saline and dextrose solution, and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions.

As used herein, the phrase "an effective amount" refers to an amount of a pharmaceutical composition of the present invention which, when administered to an animal with cancer, will decrease or inhibit tumor growth and metastasis in the animal or, alternatively, if the animal has no detectable metastasis or tumor growth, will prevent metastasis and tumor growth. When the animal is afflicted with a disease other than cancer, administration of an effective amount of a pharmaceutical composition will cause the remission of the disease or of one or more symptoms of the disease, or will prevent the worsening of one or more of the symptoms present, or will prevent the development of further symptoms. One of ordinary skill in the art can readily determine the effective amount of a pharmaceutical composition of the present invention to administer using routine experimental techniques.

Hence, in the case of cancers in which the Ras proteins have been aberrantly activated, the present invention is directed towards methods for modulating tumor growth and metastasis comprising, inter alia, the administration of an effective amount of a pharmaceutical composition of the present invention. In the case of other diseases in which Ras proteins have been aberrantly activated, the present invention is directed towards methods for modulating the severity of such diseases comprising, inter alia, the administration of an effective amount of a pharmaceutical composition of the present invention.

Preferably, administration of pharmaceutical compositions of the present invention is parenteral, e.g., via intravenous injection, but intra-arteriole, intramuscular, intradermal, subcutaneous, intraperitoneal, intraventricular, and intracranial administration are also included, without limitation. More preferably, the pharmaceutical composition may be introduced by injection into the tumor(s) being treated or into tissues surrounding the tumor(s).

In one embodiment, a pharmaceutical composition of the present invention can be delivered in a controlled release system, such as using an intravenous infusion, an implantable osmotic pump, liposomes, or other modes of administration. In a particular embodiment, a pump may be used [see Langer, Science 249:1527–1533 (1990); Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)]. In yet another embodiment, a controlled release system can be placed in proximity to the target tissues of the animal, thus requiring only a fraction of the systemic dose [see, e.g., Goodson, in Medical Applications of Controlled Release, supra, vol. 2, pp. 115–138 (1984)]. In particular, a controlled release device can be introduced into an animal in proximity to the site of inappropriate immune activation or a tumor. Other controlled release systems are discussed in Langer, Science 249:1527–1533 (1990).

The following examples are provided to describe the invention in further detail. These examples are intended to illustrate and not to limit the invention. All temperatures are given in centigrade degrees (° C.) unless otherwise noted.

EXAMPLE 1

Preparation of (R)-3-[N-(1-Hydroxymethyl-2-phenylethyl)amino]methyl]-4-nitrobenzenecarbonitrile

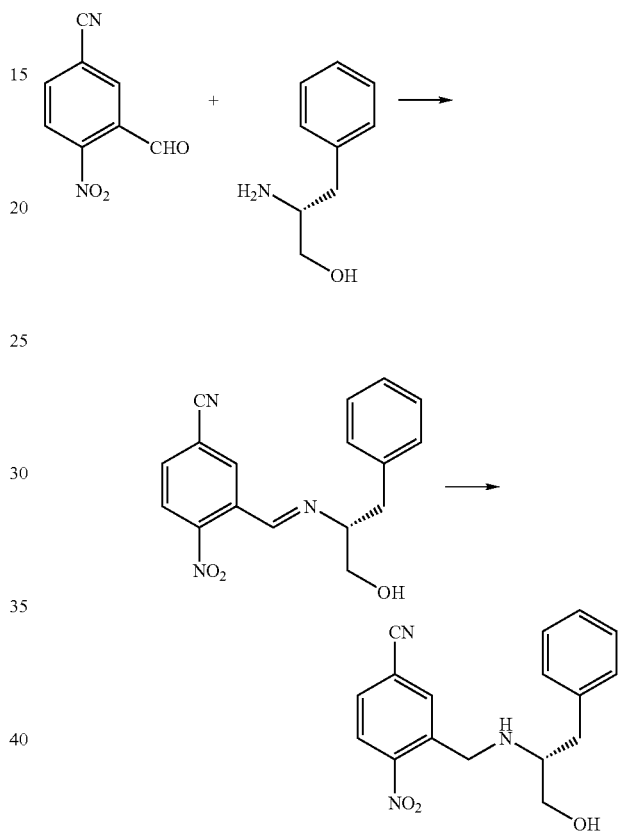

Under a nitrogen atmosphere, a solution of 5-cyano-2-nitrobenzaldehyde (2,700 g, 15.33 mol) and D-phenylalaninol (2,412 g, 15.95 mol) in dichloromethane was heated at reflux for 2 hours. After cooling the reaction mixture to 5° C., acetic acid (1,476 g, 24.58 mol) was added, followed by the portionwise addition of sodium triacetoxy borohydride (4,565 g, 85% real, 18.31 mol). The reaction mixture was warmed to room temperature and stirred at room temperature overnight, cooled to 15° C. and diluted with 1N sodium hydroxide solution (18,166 mL) while maintaining the reaction mixture temperature below 25° C. The phases were separated. The organic phase was distilled to remove dichloromethane. The pot was chased twice with tert-butyl methyl ether (2×36,360 mL). The resultant slurry was stirred overnight at 25° C., cooled to 0°–5° C., held at 5° C. for 1 hour and filtered to obtain a solid. The solid was washed twice with 10 L portions of 5° C. tert-butyl methyl ether and dried in a 30° C. vacuum oven to give the title product as a solid (3,703 g, 77% yield).

EXAMPLE 2

Preparation of (R)-N-[(5-Cyano-2-nitrophenyl)methyl]-N-[(1-hydroxymethyl)-2-phenylethyl]thiophene-2-sulfonamide

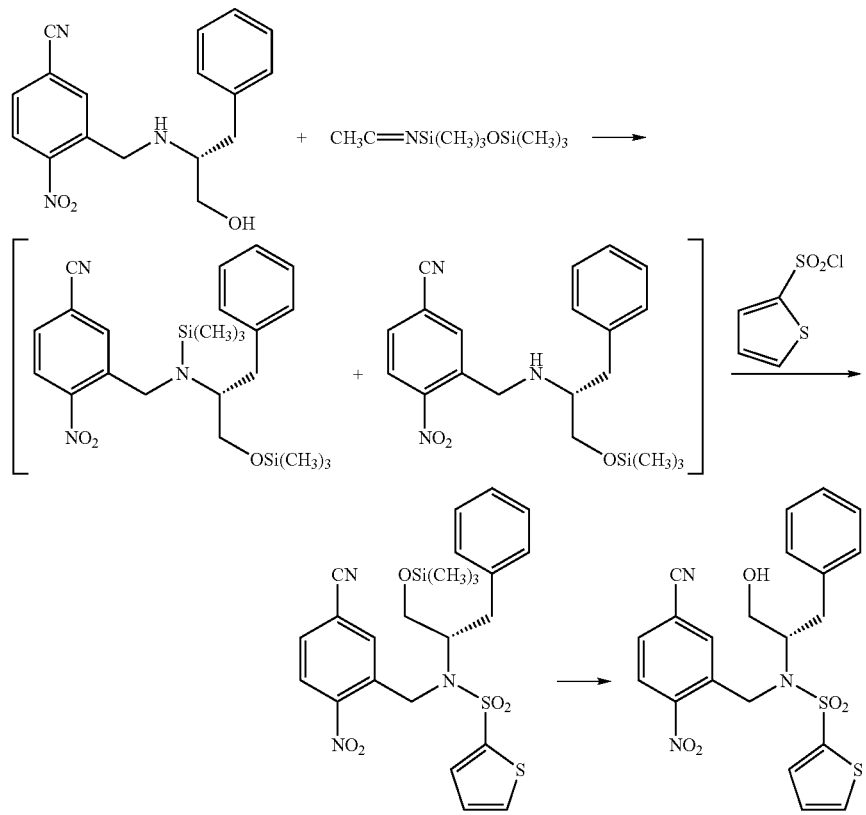

A three-necked round bottom flask equipped with a thermocouple, a nitrogen inlet, and a mechanical stirrer was charged with (R)-3-[N-(1-hydroxymethyl-2-phenylethyl)amino]methyl]-4-nitrobenzenecarbonitrile (25 g, 0.08 moles), THF (20 ml), and N-methyl morpholine (NMM) (17.8 mL, 2.0 eq). To this mixture was added N,O-bis(trimethylsilyl)acetamide (BSA) (15 mL, 0.75 eq). The reaction mixture was stirred for 30–45 min at a temperature of 20 to 30° C.; then, a solution of 2-thienylsulfonyl chloride (23.0 g, 1.5 eq) in THF (5 mL) was added with stirring while holding the reaction mixture in the same temperature range for 8 h to 16 h until the reaction was judged to be sufficiently complete by HPLC analysis. THF (200 mL), MTBE (200 mL), and water (80 mL) were added sequentially and the reaction mixture was stirred for 10–15 min before separating the phases. The organic phase was washed with water and any remaining THF solvent was exchanged for methanol through repeatedly removing portions of the THF by distillation at ambient pressure and adding fresh methanol. The cycles were reiterated until the volume of the solution was approximately 125 mL and the solvent exchange was judged to be sufficiently complete by HPLC analysis. The reaction product was crystallized by cooling the methanol solution to 20–25° C. and stirring for at least 2 h. The crystals were removed by filtration, washed with cold methanol, and dried in a vacuum oven (25 inches at 40° to 50° C.) to yield (R)-N-[5-cyano-2-nitrophenyl) methyl]-N-[(1-hydroxymethyl)-2-phenylethyl]thiophene-2-sulfonamide (30.4 g, 83.0% yield).

EXAMPLE 3

Preparation of (R)-7-Cyano-2,3,4,5-tetrahydro-3-(phenylmethyl)-4-[2(1H)-thienylsulfonyl]-1H-1,4-benzodiazepine

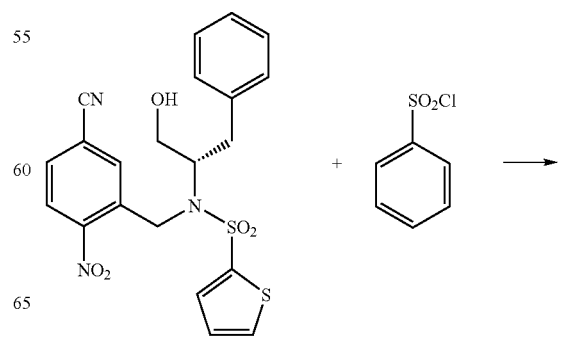

-continued

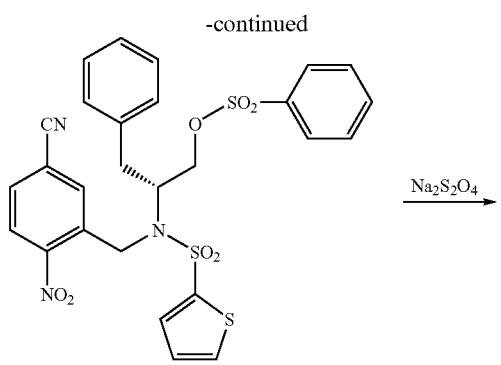

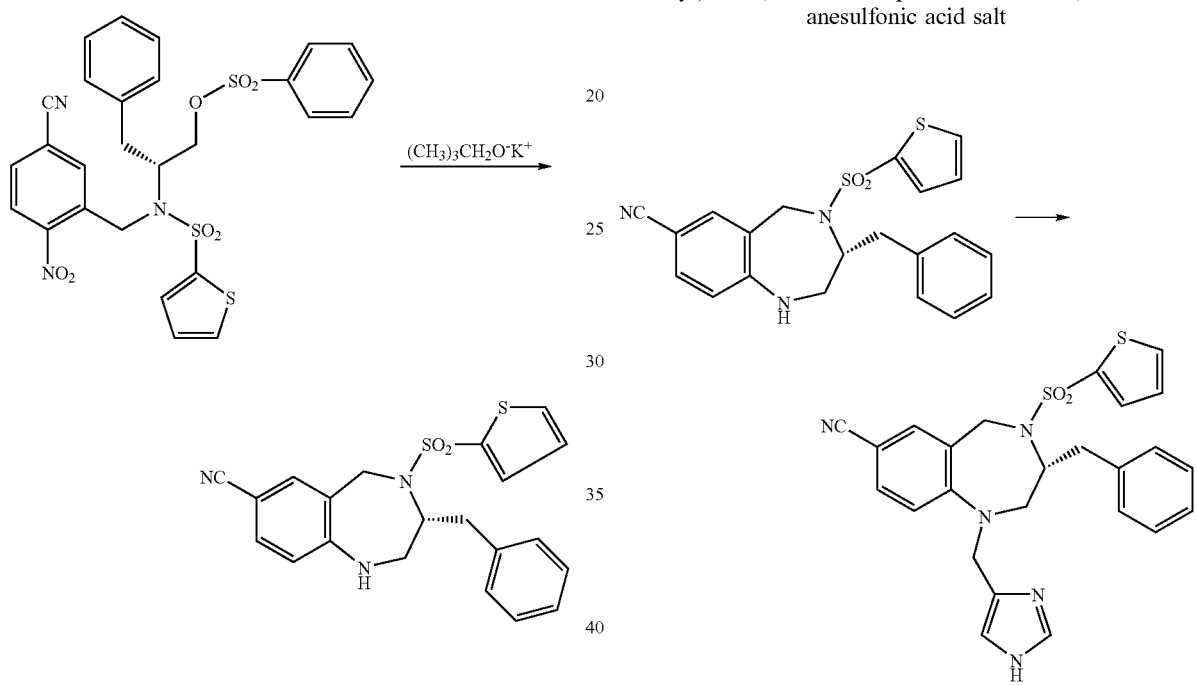

Benzenesulfonyl chloride (1,488 g, 8.42 mol) was slowly added to a mixture of (R)-N-[5-cyano-2-nitrophenyl)methyl]-N-[(1-hydroxymethyl)-2-phenylethyl]thiophene-2-sulfonamide (3,500 g, 7.66 mol), 4-dimethylaminopyridine (84.2 g, 0.69 mol) and triethylamine (1,085 g, 10.72 mol) in dichloromethane. The resultant reaction mixture was stirred at room temperature for 3 hours, diluted with tetrahydrofuran and cooled to 10°–15° C. A sodium dithionite solution (prepared from 6,270 g of 85% sodium dithionite and 35,000 g of water) was added to the cooled reaction mixture at such a rate as to maintain the reaction mixture temperature below 15° C. After the addition was complete, the reaction mixture was warmed to and stirred at room temperature overnight, treated with concentrated hydrochloric acid to a pH of about 1.5–2.0, and the phases were separated. The organic phase was washed with brine and concentrated in vacuo. The pot was chased with toluene and the resultant residue was diluted with tetrahydrofuran, cooled to 0°–5° C., treated with a potassium t-amylate solution (5,000 mL of a 25 wt % solution in toluene, 9.96 mol) over 20 minutes while maintaining the reaction mixture temperature at 0°–5° C., stirred for 30 minutes, treated with a 5 wt % potassium monobasic phosphate solution (17,500 mL) while maintaining the reaction mixture temperature at 5°–10° C., stirred for 5 minutes, and the phases were separated. The organic phase was concentrated in vacuo, diluted with methanol (31,500 mL), decolorized with charcoal, and concentrated in vacuo to a volume of about 9,400 mL. The resultant solution was warmed to 55°–60° C., cooled to about 50° C., seeded, cooled to and held at room temperature overnight, cooled to and held at 0° C. for 2 hours, and filtered to obtain a solid. The solid was washed with a 9:1 methanol/water solution at 4° C., and dried in a 45° C. vacuum oven to give the title product as a solid (2,195 g, 70% yield).

EXAMPLE 4

Preparation of (R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile, methanesulfonic acid salt (R)-2,3,4,5-tetrahydro-3-(phenylmethyl)-4-(2-thienylsulfonyl)-1H-1,4-benzodiazepine-7-carbonitrile (10 g) and imidazole-4-carboxaldehyde (2.6 g) were mixed in toluene (30 mL) at 20 to 25° C. To this stirred slurry, first trifluoroacetic acid (9.4 mL) and then trifluoroacetic acid anhydride (4.2 mL) were added sequentially while maintaining the temperature below 30° C. The biphasic mixture was vigorously stirred at 20 to 25° C. for 30 minutes. Triethylsilane (4.6 mL) was then added and the reaction mixture was stirred at 20 to 25° C. until the reaction was determined to be complete (>99%) according to HPLC assay. Ethanol-water (99:1, 150 mL) was added and the resulting solution was polish-filtered, e.g., through filter paper or a celite bed. The solution was heated to 60° C. Methanesulfonic acid (1.8 mL) was added at this temperature and a white slurry formed. The slurry was cooled to 20 to 25° C. over 1 hour and stirred for an additional 1 hour. The resulting white crystalline solid was filtered and washed with cold anhydrous ethanol (50 mL). The wet cake was dried in a vacuum oven at 70° C. until the loss on drying was <0.5% to afford the title product as a white, crystalline substance (13.2 g, 92.3% yield; HPLC, area percent>99).

EXAMPLE 5

Alternative Preparation of (R)-7-Cyano-2,3,4,5-tetrahydro-3-(phenylmethyl)-4-[2(1H)-thienylsulfonyl]-1-H-1,4-benzodiazepine

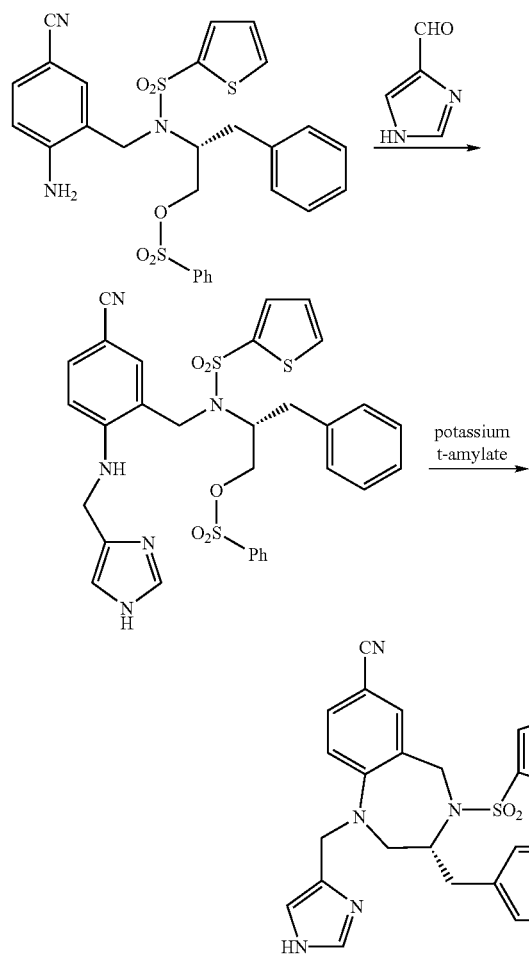

1. Preparation of benzenesulfonic acid 2-[{5-cyano-2-[(1H-imidazol-4-ylmethyl)-amino]-benzyl}-(thiophene-2-sulfonyl)-amino]-3-phenyl-propyl ester To a suspension of N-(2-amino-5-cyanophenyl)methyl]-N-[1R)-1-1(phenylmethyl)-2-[(phenylsulphonyl)oxy]ethyl]-2-thiophenesulfonamide (7.3 g, 12.9 mmol, as prepared in Example 3 and below) and 4-formyl imidazole (1.4 g, 14.1 mmol) in methylene chloride (25 mL) was added trifluroacetic acid (5 mL). The resulting clear solution was stirred at room temperature (r.t.) for half-hour under nitrogen, followed by addition of triethylsilane. The mixture was stirred at rt. for 3 h. The solvent was evaporated and the residue was dissolved in ethyl acetate-$H_2O$ (70 mL/50 mL). Potassium tribasic phosphate (about 7.5 g) was added until pH 8 at 0° C. The organic layer was separated, washed with half-saturated brine (50 mL), brine (50 mL), dried over sodium sulfate, filtered, and concentrated to gave an oil. Methyl t-butylether (30 mL) was added to this oil and the mixture was stirred at r.t. for 2 h. The resulting white solid was filtered and washed with methyl t-butylether (10 mL), dried under vacuum for overnight to gave 8.1 g of benzenesulfonic acid 2-[{5-cyano-2-[(1H-imidazol-4-ylmethyl)-amino]-benzyl}-(thiophene-2-sulfonyl)-amino]-3-phenyl-propyl ester (97% yield).

2. Preparation of (R)-7-cyano-2,3,4,5-tetrahydro-3-(phenylmethyl)-4-[2(1H)-thienylsulfonyl]-1H-1,4-benzodiazepine Benzenesulfonic acid 2-[{5-cyano-2-[(1H-imidazol-4-ylmethyl)-amino]-benzyl}-(thiophene-2-sulfonyl)-amino]-3-phenyl-propyl ester (1.15 g, 1.8 mmol) was dissolved in tetrahydrofuran (10 mL) and the resulting solution was cooled in an-ice bath. Potassium t-amylate (25 wt % in toluene, 1.52 g, 3.0 mmol) was added dropwise over a 20 min period to this solution at 0° C. under nitrogen. The resulting yellow mixture was stirred at 0° C. for 3 h. The reaction mixture was partitioned between ethyl acetate (10 mL) and $H_2O$ (10 mL). The organic layer was separated, washed with half-saturated brine (10 mL) and brine (10 mL), dried over sodium sulfate, filtered and concentrated to gave 0.9 g of red solid. This solid was dissolved in ethyl acetate (30 mL). Charcoal (0.2 g) and silica-gel (1 g) were added. After being stirred at r.t. for 1 h, the solids were filtered through celite and washed with ethyl acetate (10 mL). Concentration of the filtrate gave 0.70 g of (R)-7-cyano-2,3,4,5-tetrahydro-3-(phenylmethyl)-4-[2(1H)-thienylsulfonyl]-1H-1,4-benzodiazepine (77% yield) as a yellow solid.

3. Preparation of N-(2-amino-5-cyanophenyl)methyl]-N-[1R)-1-1(phenylmethyl)-2-[(phenylsulphonyl)oxy]ethyl]-2-thiophenesulfonamide

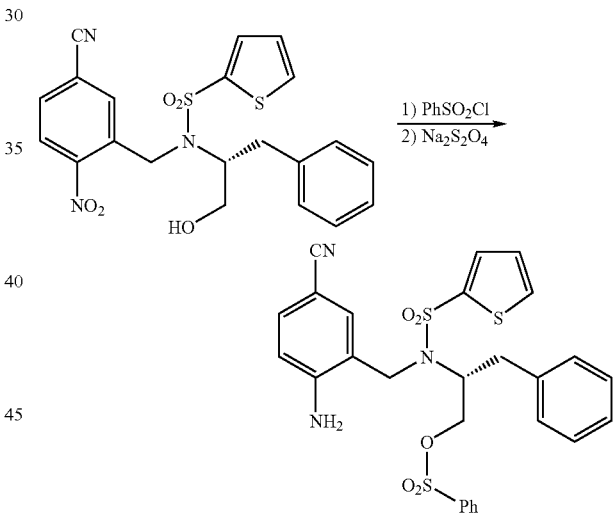

To a 500 mL-flask equipped with a magnetic stirrer were added compound (R)-N-[5-cyano-2-nitrophenyl)methyl]-N-[(1-hydroxymethyl)-2-phenylethyl]thiophene-2-sulfonamide (17.0 g, 37.2 mmol), 170 mL of methylene chloride, triethylamine (5.6 g, 55.8 mmol), and 4-dimethylaminopyridine (0.9 g, 7.4 mmol), resulting in a yellow solution. Benzenesulfonyl chloride (7.88 g, 44.6 mmol) was added dropwise to this solution over a 30 min. period at room temperature under nitrogen. The mixture was stirred at room temperature (r.t.) under nitrogen for 5 h. The solvent was removed on a rotary evaporator at r.t. The residue was treated with ethyl acetate (200 mL) and 1N hydrochloric acid (100 mL). The organic layer was separated, washed with half saturated brine (150 mL), saturated sodium bicarbonate (150 mL) and saturated brine (150 mL), and dried over anhydrous sodium sulfate. Concentration of the organic solution on a rotary evaporator gave a yellow amorphous solid (22.5 g) after drying overnight under vacuum. The solid was dissolved in tetrahydrofuran (200 mL). To this solution was added a solution of sodium hydrosulfite (23.3 g, 85%, 11.3 mmol) in water (200 mL) at room temperature. The reaction mixture was then stirred at 50° C. (oil bath) under nitrogen for 2 h. Tetrahydrofuran was removed on a rotary evaporator. Ethyl acetate (200 mL) was added to the residue. Solid potassium phosphate (16 g) was added to the mixture until pH=9. The organic layer was separated, washed with half saturated brine (2×150 mL), dried over anhydrous sodium sulfate and concentrated to give a yellow solid. This solid was dissolved in methylene chloride (50 mL) and was filtered through a silica-gel pad (60 g, pre-wetted with methylene chloride) which was eluted with ethyl acetate-hexane (3:1, 410 mL). Evaporation of the elute gave 19.3 g (93.5% yield) of N-(2-amino-5-cyanophenyl)methyl]-N-[1R]-1-1(phenylmethyl)-2-[(phenylsulphonyl)oxy]ethyl]-2-thiophenesulfonamide as a yellow amorphous solid after drying overnight at room temperature in vacuo.

The invention claimed is:

1. A process for the preparation of a compound of formula I (I)

wherein

R is Cl, Br, CN, optionally substituted phenyl or optionally substituted 2-, 3- or 4-pyridyl;
$R_1$ is optionally substituted lower alkyl, optionally substituted aryl or optionally substituted heterocyclo;
$R_2$ is optionally substituted lower alkyl or optionally substituted aralkyl;
Z is CO or $SO_2$;
A is hydrogen or, optionally, —$(CH_2)_n$—[imidazole with $R_3$];

$R_3$ is hydrogen or lower alkyl; and
n is 1 or 2, which process comprises the steps of:
a) reacting a compound of formula XII (XII)

wherein R, $R_1$, $R_2$, and Z are as recited hereinabove and $R_5$ is lower alkyl or optionally substituted phenyl, with a base to form a compound of formula I wherein A is hydrogen; and b) optionally reacting the product of step a) with a heterocyclic aldehyde of the formula XIII (XIII)

[imidazole]—$(CH_2)_{n-1}$CHO, wherein $R_3$ and n are as recited hereinabove, under reductive alkylation conditions to form a compound of formula I wherein A is —$(CH_2)_n$—[imidazole with $R_3$].

2. The process according to claim 1 wherein
R is CN;
$R_1$ is optionally substituted lower alkyl, optionally substituted phenyl optionally substituted 2-thienyl or optionally substituted 1-piperidinyl;
$R_2$ is optionally substituted benzyl;
Z is CO or $SO_2$;
A is hydrogen or, optionally, —$(CH_2)_n$—[imidazole with $R_3$]; and $R_3$ is hydrogen or methyl.

3. The process according to claim 1 wherein
R is CN;
$R_1$ is n-propyl, n-butyl, 3-methoxypropyl, 2-thienyl, 5-bromo-2-thienyl, phenyl, 4-methoxyphenyl or 1-piperidinyl;
$R_2$ is benzyl;
Z is $SO_2$; and
A is —$CH_2$—[imidazole NH].

4. The process according to claim 1 for the preparation of a compound selected from the group consisting of
(R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile;
(R)-2,3,4,5-tetrahydro-3-(phenylmethyl)-4-(2-thienylsulfonyl)-1H-1,4-benzodiazepine-7-carbonitrile;

(R)-7-cyano-2,3,4,5-tetrahydro-1-(1H-imidazol-4-ylmethyl)-4-(1-oxobutyl)-3-(phenylmethyl)-1H-1,4-benzodiazepine;

(R)-7-cyano-2,3,4,5-tetrahydro-4-(1-oxobutyl)-3-(phenylmethyl)-1H-1,4-benzodiazepine;

(R)-4-[(5-bromo-2-thienyl)sulfonyl]-7-cyano-2,3,4,5-tetrahydro-1-(1H-imidazol-4-ylmethyl)-3-(phenylmethyl)-1H-1,4-benzodiazepine;

(R)-4-[(5-bromo-2-thienyl)sulfonyl]-7-cyano-2,3,4,5-tetrahydro-3-(phenylmethyl)-1H-1,4-benzodiazepine;

(R)-7-cyano-2,3,4,5-tetrahydro-1-(1H-imidazol-4-ylmethyl)-4-[(4-methoxy-phenyl)sulfonyl]-3-(phenylmethyl)-1H-1,4-benzodiazepine;

(R)-7-cyano-2,3,4,5-tetrahydro-4-[(4-methoxyphenyl)sulfonyl]-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(phenylsulfonyl)-1H-1,4-benzodiazepine;

(R)-7-cyano-2,3,4,5-tetrahydro-3-(phenylmethyl)-4-(phenylsulfonyl)-1H-1,4-benzodiazepine;

(R)-7-cyano-2,3,4,5-tetrahydro-1-(1H-imidazol-4-ylmethyl)-3-(phenylmethyl)-4-(propylsulfonyl)-1H-1,4-benzodiazepine;

(R)-7-cyano-2,3,4,5-tetrahydro-3-(phenylmethyl)-4-(propylsulfonyl)-1H-1,4-benzodiazepine;

(R)-4-(butylsulfonyl)-7-cyano-2,3,4,5-tetrahydro-1-(1H-imidazol-4-ylmethyl)-3-(phenylmethyl)-1H-1,4-benzodiazepine;

(R)-4-(butylsulfonyl)-7-cyano-2,3,4,5-tetrahydro-3-(phenylmethyl)-1H-1,4-benzodiazepine;

(R)-7-cyano-2,3,4,5-tetrahydro-1-(1H-imidazol-4-ylmethyl)-3-(phenylmethyl)-4-(1-piperidinylsulfonyl)-1H-1,4-benzodiazepine;

(R)-7-cyano-2,3,4,5-tetrahydro-3-(phenylmethyl)-4-(1-piperidinylsulfonyl)-1H-1,4-benzodiazepine;

(R)-4-(3-methoxypropylsulfonyl)-7-cyano-2,3,4,5-tetrahydro-1-(1H-imidazol-4-ylmethyl)-3-(phenylmethyl)-1H-1,4-benzodiazepine; and (R)-4-(3-methoxypropylsulfonyl)-7-cyano-2,3,4,5-tetrahydro-3-(phenylmethyl)-1H-1,4-benzodiazepine.

5. The process according to claim 1 for the preparation of
(R)-2,3,4,5-tetrahydro-1-(1H-imidazol-4-ylmethyl)-3-(phenylmethyl)-4-(2-thienylsulfonyl)-1H-1,4-benzodiazepine-7-carbonitrile.

6. The process according to claim 1 for the preparation of
(R)-2,3,4,5-tetrahydro-3-(phenylmethyl)-4-(2-thienylsulfonyl)-1H-1,4-benzodiazepine-7-carbonitrile.

7. The process according to claim 1 wherein $R_5$ is optionally substituted phenyl.

8. The process according to claim 1 wherein step (a) is conducted in the presence of a solvent selected from the group consisting of an ether, an aromatic hydrocarbon, a halogenated aromatic hydrocarbon, a halogenated alkane, an N,N-dialkylamide and N-methylpyrrolidinone and mixtures thereof.

9. The process according to claim 1 wherein the base in step (a) is selected from the group consisting of an alkali metal $C_1$–$C_6$alkoxide, an alkali metal dialkylamide, an alkali metal hydride and an alkali metal carbonate.

10. The process according to claim 1 wherein the reductive alkylation of step (b) comprises reacting the formula I compound wherein A is hydrogen and the aldehyde of formula XIII with: (1) an alkali metal borohydride in the presence of an acid, or (2) a hydrotrialkylsilane in the presence of an acid and optionally, an acid anhydride.

11. The process according to claim 1 wherein the steps (a) and (b) are reversed to provide a process comprising first reacting the compound of formula XII with the aldehyde of formula XIII to form a compound of formula XIV:

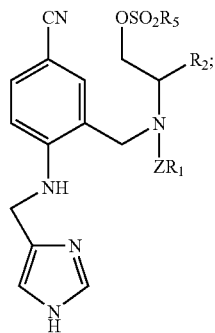

(XIV)

then reacting the compound of formula XIV with a base to effect a ring closure;

thereby forming a compound of formula I wherein A is

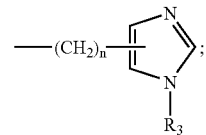

and n, $R_1$, $R_2$, $R_3$, and $R_5$ are as defined in claim 1.

* * * * *

UNITED STATES PATENT AND TRADEMARK OFFICE
CERTIFICATE OF CORRECTION

PATENT NO. : 7,074,921 B2  Page 1 of 1
APPLICATION NO. : 10/292093
DATED : July 11, 2006
INVENTOR(S) : Kronenthal et al.

It is certified that error appears in the above-identified patent and that said Letters Patent is hereby corrected as shown below:

The paragraph at column 2, lines 10-14 should be replaced with the following rewritten paragraph:
--It has also been reported that FPTase inhibitors are also inhibitors of proliferation of vascular smooth muscle cells and are, therefore, useful in the prevention and therapy of arteriosclerosis and diabetic disturbance of blood vessels (Japanese Patent 7-112930).--

The paragraph at column 7, lines 23-27 should be replaced with the following rewritten paragraph:
--Reductive aminations such as those performed in step (a) are disclosed in commonly assigned U.S. Patent No. 6,100,395, and U.S. Patent No. 6,949,642 the entire disclosures of which are herein incorporated by reference.--

Signed and Sealed this

Twenty-first Day of August, 2007

JON W. DUDAS
*Director of the United States Patent and Trademark Office*